United States Patent
Debijl

(10) Patent No.: US 8,941,501 B1
(45) Date of Patent: Jan. 27, 2015

(54) SYSTEM TO PREVENT DRUNKEN DRIVING

(71) Applicant: Travis Debijl, Northbridge (AU)

(72) Inventor: Travis Debijl, Northbridge (AU)

( * ) Notice: Subject to any disclaimer, the term of this patent is extended or adjusted under 35 U.S.C. 154(b) by 36 days.

(21) Appl. No.: 13/949,488

(22) Filed: Jul. 24, 2013

(51) Int. Cl.
*G08B 23/00* (2006.01)
*A45C 11/32* (2006.01)

(52) U.S. Cl.
CPC .................................... *A45C 11/32* (2013.01)
USPC ......................................... 340/576; 340/522

(58) Field of Classification Search
USPC ................................................ 340/576, 522
See application file for complete search history.

(56) References Cited

U.S. PATENT DOCUMENTS

| | | |
|---|---|---|
| 5,426,415 A | 6/1995 | Prachar et al. |
| 6,075,444 A | 6/2000 | Sohege et al. |
| D540,209 S | 4/2007 | Mobley et al. |
| 7,204,335 B2 | 4/2007 | Stewart et al. |
| 7,299,890 B2 | 11/2007 | Mobley et al. |
| 7,570,172 B2 | 8/2009 | Kamiki |
| 2005/0099310 A1 | 5/2005 | Jones |
| 2005/0230175 A1* | 10/2005 | Brown et al. .................. 180/272 |
| 2008/0196963 A1 | 8/2008 | Karlsson |

OTHER PUBLICATIONS www.alcotest.com, AL-2500, Jul. 23, 2013, 12:35:45pm.

* cited by examiner

*Primary Examiner* — Shirley Lu

(57) ABSTRACT

A self-policing system for preventing oneself from drunk driving features a key for inserting into an ignition switch of an automobile and a base. A base anterior end features a keyhole for receiving the key. A barbed first key camp is operatively connected to a first solenoid located in a base anterior cavity and is biased via a first spring. A barbed second key clamp is operatively connected to a second solenoid boated in the base anterior cavity and is biased via a second spring. A base posterior end features a breathing aperture located on a tip. A base posterior cavity features an alcohol sensor and a power supply each operatively connected to a microprocessor.

3 Claims, 6 Drawing Sheets

SYSTEM TO PREVENT DRUNKEN DRIVING

FIELD OF THE INVENTION

The present invention relates to devices used to prohibit drunken driving, or more specifically, blood alcohol concentration detecting devices used to prohibit drunken driving.

BACKGROUND OF THE INVENTION

The problem of driving under the influence of alcohol or drugs continues to be a major issue in society even as penalties have continued to stiffen. Devices are sometimes installed on a car of a habitual offender as required by law to prevent them from driving when under the influence of alcohol or drugs. The present invention features a self-policing system for preventing oneself from drunk driving.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

The present invention features a self-policing system for preventing oneself from drunk driving. In some embodiments, the system comprises a key for inserting into an ignition switch of an automobile for operation.

In some embodiments, the system comprises a base. In some embodiments, a base anterior end comprises a keyhole for receiving the key. In some embodiments, a barbed first key clamp operatively connected to a first solenoid is located in a base anterior cavity and biased via a first spring. In some embodiments, a barbed second key clamp operatively connected to a second solenoid is located in the base anterior cavity and biased via a second spring.

In some embodiments, a base posterior end comprises a breathing aperture located on a tip thereon. In some embodiments, a base posterior cavity comprises an alcohol sensor and a power supply each operative connected to a microprocessor located therein.

In some embodiments, a key is located in the anterior cavity via the keyhole and secured via the first spring biased barbed first key clamp interfacing with a key first side keycut and the second spring biased barbed second key clamp interfacing with a key second side keycut. In some embodiments, to release the key from the base anterior cavity, a user breathes into the breathing aperture. The alcohol sensor detects a blood alcohol content by volume in a breath of the user. If the blood alcohol content is below a blood alcohol content limit, the key is released via movement of the first solenoid and the second solenoid.

DESCRIPTION OF PREFERRED EMBODIMENTS

Figure 1:
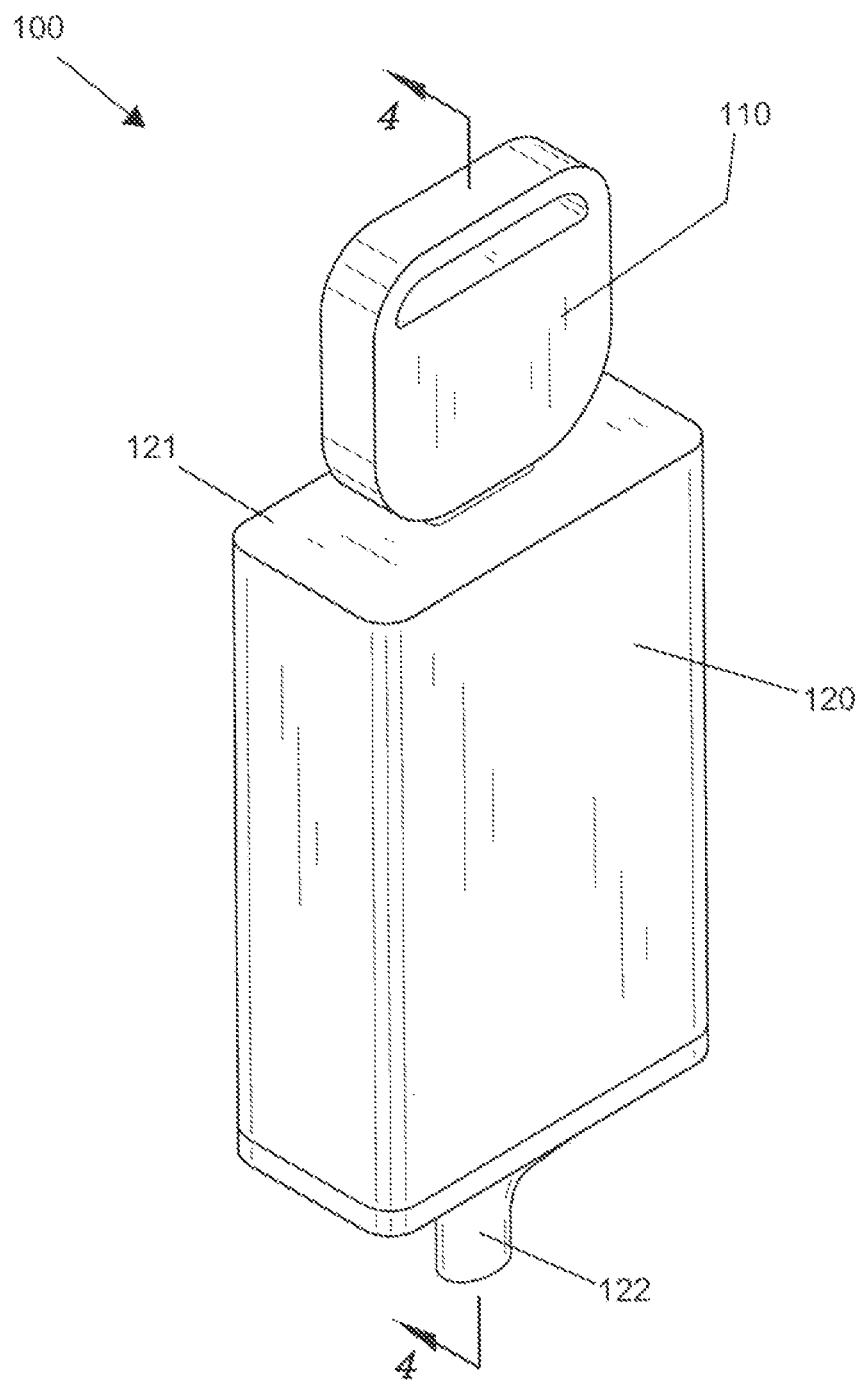
FIG. 1 shows a perspective view of the present invention.
Figure 2:
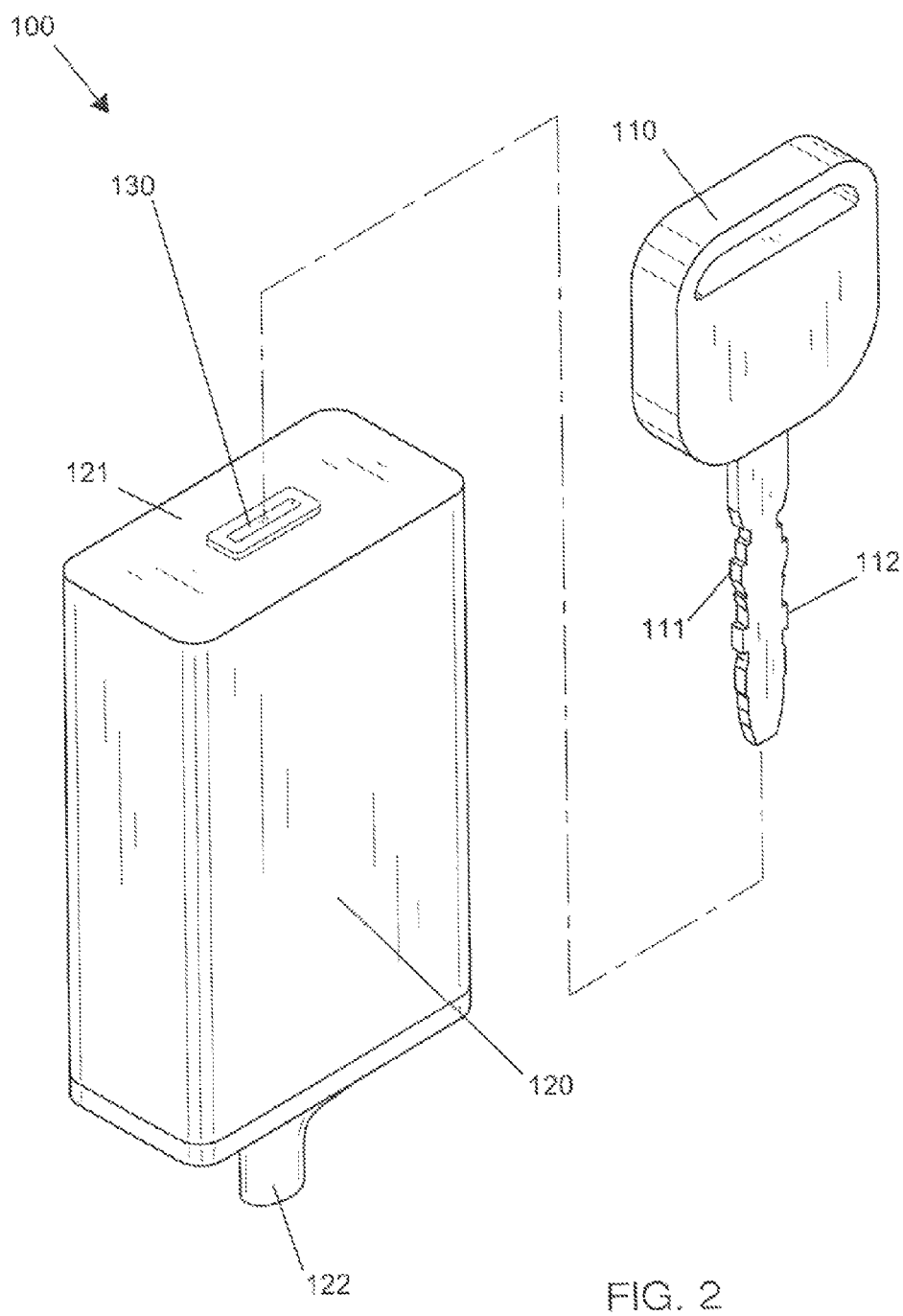
FIG. 2 shows a perspective view of the key and the base of the present invention.
Figure 3:
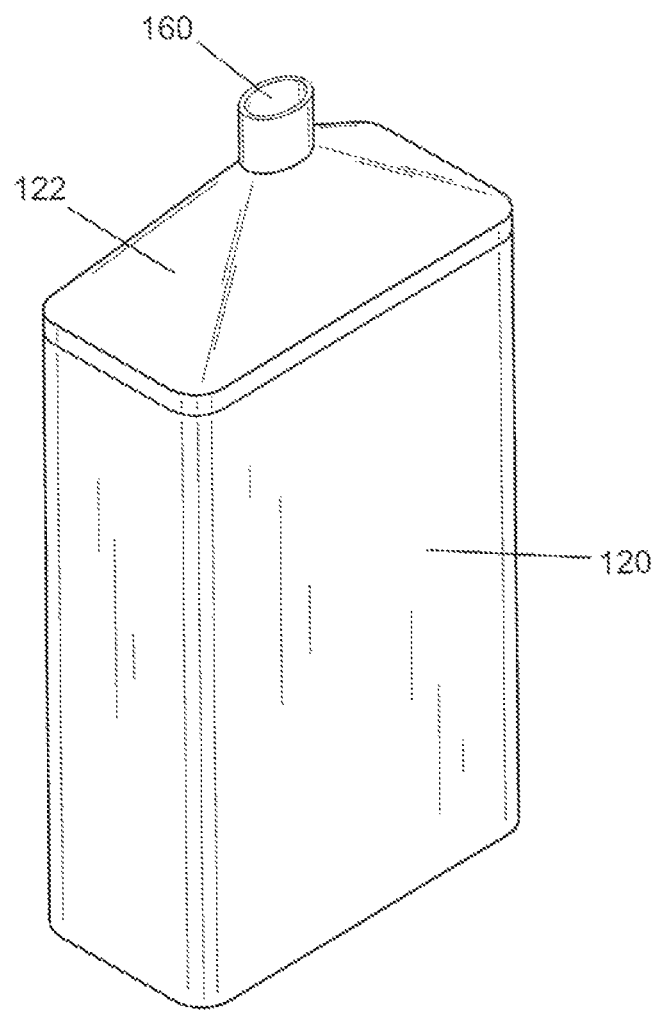
FIG. 3 shows a perspective view of the base of the present invention featuring the base posterior end.
Figure 4:
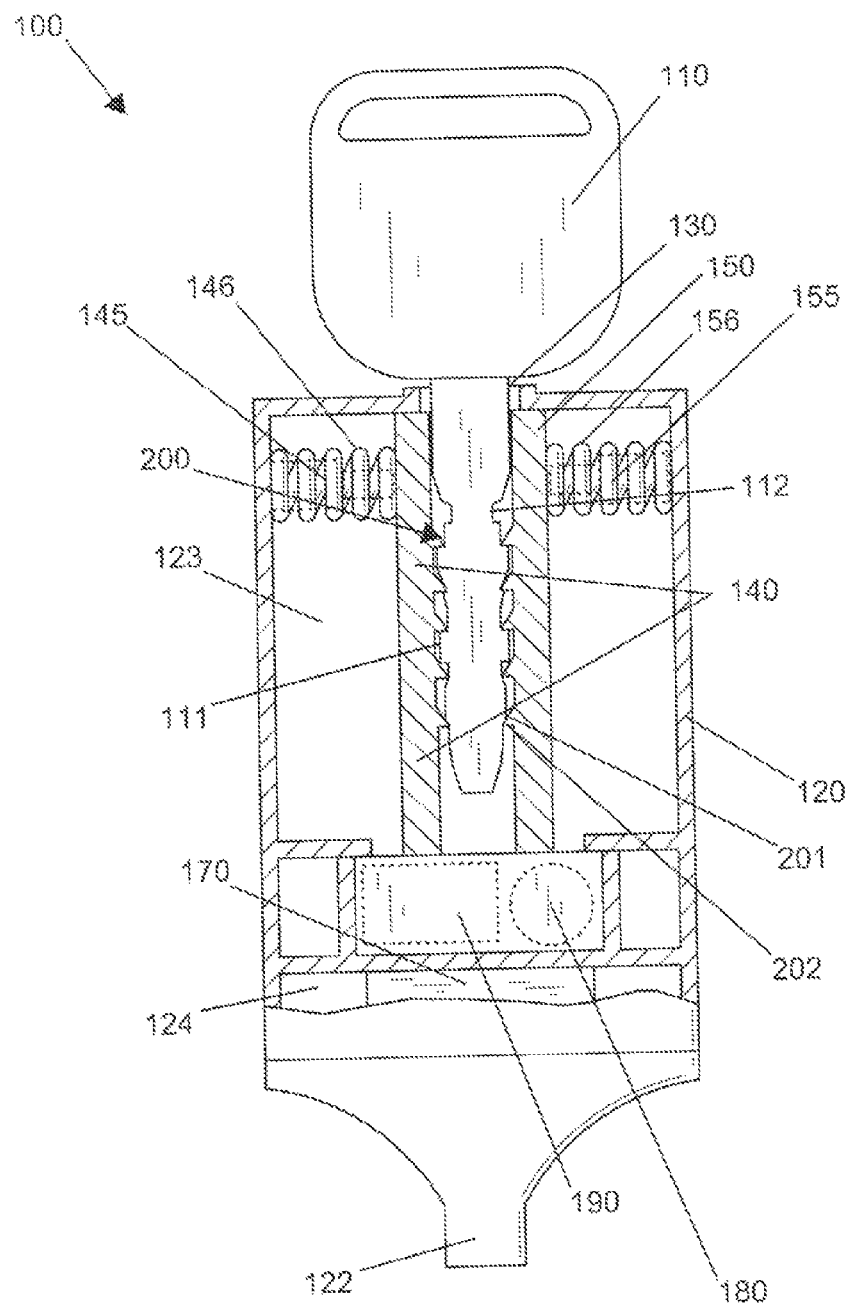
FIG. 4 shows a cutaway view of the present invention in a secured position.
Figure 5:
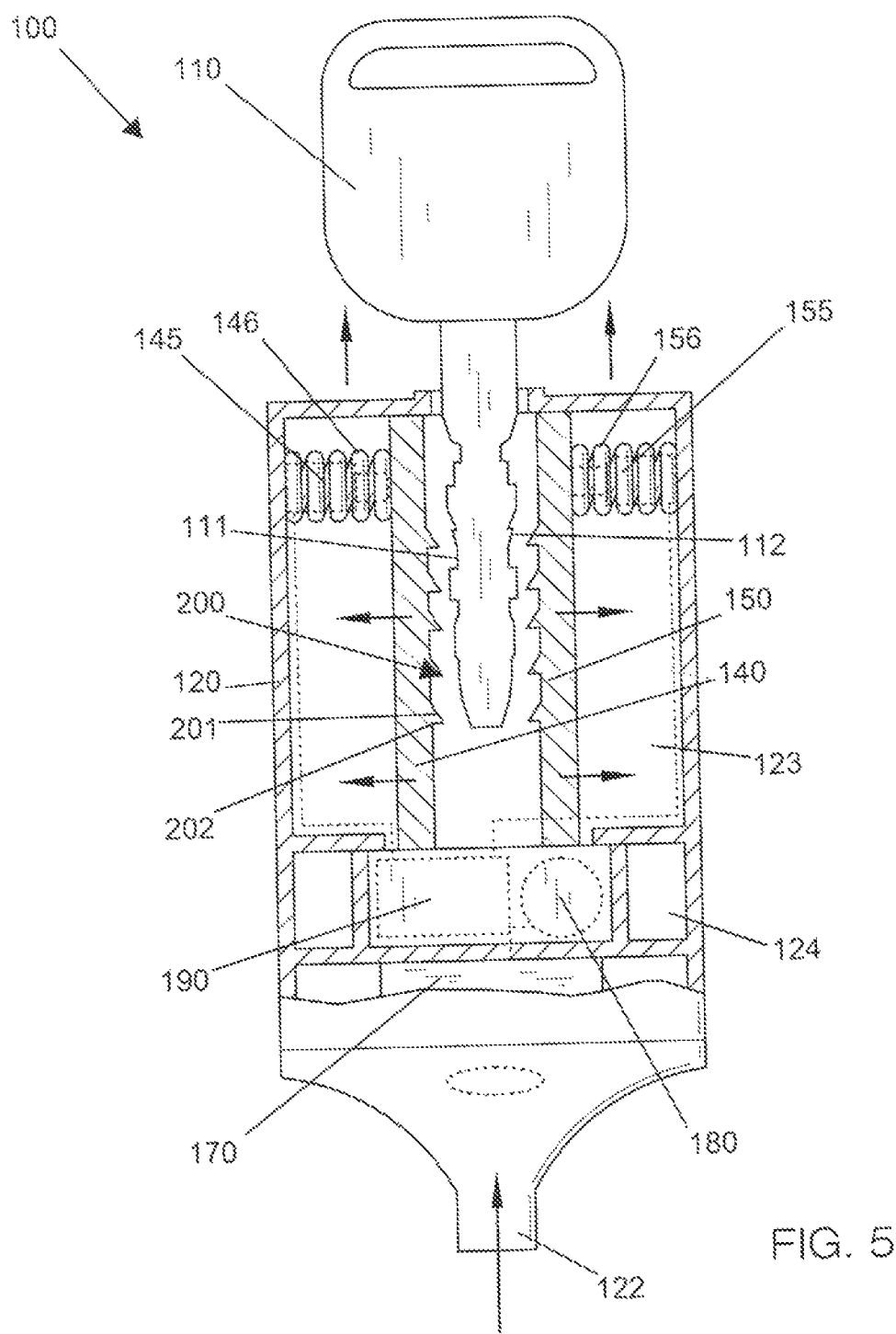
FIG. 5 shows a cutaway view of the present invention in a released position featuring the first key clamp, the second key clamp, the alcohol sensor, the power supply and the microprocessor schematically connected.
Figure 6:
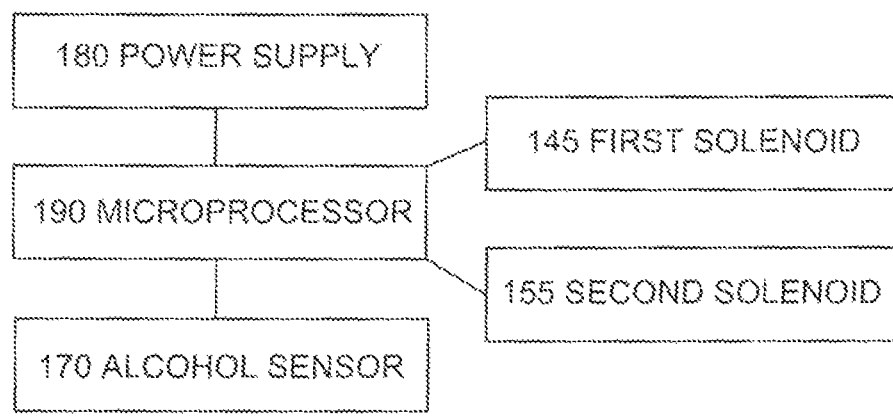
FIG. 6 shows a schematic view of the present invention.

Following is a list of elements corresponding to a particular element referred to herein:

100 Drunken driving prevention system
110 Key
111 Key first side keycut
112 Key second side Keycut
120 Base
121 Base anterior end
122 Base posterior end
123 Base anterior cavity
124 Base posterior cavity
130 Keyhole
140 First key clamp
145 First solenoid
146 First spring
150 Second key clamp
155 Second solenoid
156 Second spring
160 Breathing aperture
170 Alcohol sensor
160 Power supply
190 Microprocessor
200 Barb
201 Barb anterior side
202 Barb posterior side Referring now to FIG. 1-6, the present invention features a self-policing drunken driving prevention system (100). In some embodiments, the system (100) comprises a key (110) for inserting into an ignition switch of an automobile for operation.

In some embodiments, the system (100) comprises a base (120) having a planar base anterior end (121), a conical base posterior end (122), a base anterior cavity (123) located within close to the base anterior end (121), and a base posterior cavity (124) located within close to the base posterior end (122).

In some embodiments, the base anterior end (121) comprises a keyhole (130) located thereon for receiving the key (110). In some embodiments, the keyhole (130) is fluidly connected to the base anterior cavity (123) in some embodiments, a barbed first key clamp (140) operatively connected to a first solenoid (145) is located in the base anterior cavity (123) and outwardly biased via a first spring (146). In some embodiments, a barbed second key clamp (150) operatively connected to a second solenoid (155) is located in the base anterior cavity (123) and outwardly biased via a second spring (156). In some embodiments, the first key clamp (140) and the second key clamp (150) are designed to fit many keys (110). In some embodiments, the first key clamp (140) and the second key clamp (150) are adapted to fit a single key (110).

In some embodiments, the base posterior end (122) comprises a breathing aperture (160) located on a tip thereon. In some embodiments, the breathing aperture (160) is fluidly connected to the base posterior cavity (124). In some embodiments, the base posterior cavity (124) comprises an alcohol sensor (170) and a power supply (180) each operatively connected to a microprocessor (190) located therein, in some embodiments, the microprocessor (190) is operatively connected to the first solenoid (145) and the second solenoid (155) in some embodiments, the microprocessor (190) and the power supply (180) are physically separated from the alcohol sensor (170) via a barrier.

In some embodiments, a key (110) is inserted into the base anterior cavity (123) via the keyhole (130). In some embodiments, the key (110) is secured via the first spring (146) biased barbed first key clamp (140) interfacing with a key first side keycut (111) and a second spring (156) biased barbed second key clamp (150) interfacing with a key second side keycut (112). In some embodiments, in a secured position the key (110) is held in the base anterior cavity (123), with the first key clamp (140) and the second key clamp (150) clamping the key. In some embodiments, the key (110) is inserted through the keyhole (130) and clicks past the barbs (200) on the first key clamp (140) and the second key clamp (150) until the key (110) is in position.

In some embodiments, to release the key (110) from the base anterior cavity (123) a user breathes into the breathing aperture (160) located in the base posterior cavity (124). In some embodiments, the alcohol sensor (170) detects a blood alcohol content by volume in a breath of the user. In some embodiments, if the blood alcohol content is below a blood alcohol content limit, the key (110) is released via retraction of the first solenoid (145) attached to the first key clamp (140) and the second solenoid (155) attached to the second key clamp (150) via the microprocessor (190)

In some embodiments, the blood alcohol content limit is 0.05 by volume or 0.05%. In some embodiments, the blood alcohol content limit is 0.08 by volume or 0.08%.

In some embodiments, the first key clamp (140) and the second key clamp (150) comprise barbs (200). In some embodiments, each barb (200) comprises a sloped barb anterior side (201) and a perpendicular barb posterior side (202) for slidably allowing entrance of the key (110) and for limiting exit of the key (110) unless the blood alcohol content is below the blood alcohol content limit.

In some embodiments, the key (110) is disposed in the base anterior cavity (123) via the keynote (130). In some embodiments, the key (110) is slid into position and secured via the first spring (146) biased barbed first key clamp (140) interfacing with a key first side keycut (111) and the second spring (156) biased barbed second key clamp (150) interfacing with a key second side keycut (112). In some embodiments, in a secured position the key (110) is held in the base anterior cavity (123), via the first key clamp (140) and the second key clamp (150) clamping the key.

In some embodiments, to release the key (110) from the base anterior cavity (123) a user breathes into the breathing aperture (160) disposed in the base posterior cavity (124). In some embodiments, the alcohol sensor (170) detects a blood alcohol content by volume in a breath of the user, in some embodiments, the microprocessor (ISO) analyzes the blood alcohol content with respect to a blood alcohol limit. In some embodiments, if the blood alcohol content is below the blood alcohol content limit, the microprocessor (190) sends a signal to the first solenoid (145) and the second solenoid (155) to retract for a period of time. In some embodiments, the period of time is one second. In some embodiments, the period of time is three seconds. In some embodiments, the period of time is five seconds or more In some embodiments, upon retraction of the first solenoid (145), the first key clamp (140) slides away from the key first side keycut (111) of the key (110). In some embodiments, upon retraction of the second solenoid (155), the second key clamp (150) slides away from the key second side keycut (112). In some embodiments, the key (110) is able to be pulled from the keynote (130). In some embodiments, after a period of time, the first solenoid (145) and the second solenoid (155) release from a retracted position.

As used herein, the term "about" refers to plus or minus 10% of the referenced number.

The disclosures of the following U.S. Patents are incorporated in their entirety by reference herein: U.S. Pat. No. D 540,209; U.S. Patent Pub. No 2008/0196963; U.S. Patent Pub. No. 2005/0230175; U.S. Patent Pub. No. 2005/0099310; U.S. Pat. No. 7,299,890; U.S. Pat. No. 7,204,335, U.S. Pat. No. 6,075,444; and U.S. Pat. No. 5,426,415.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended m any way to limit the scope of the claims to the particular features having the corresponding reference numbers in the drawings.

What is claimed is:

1. A self-policing drunken driving prevention system, wherein the system comprises:
  (a) a key for inserting into an ignition switch of an automobile for operation; and
  (b) a base having a planar base anterior end, a conical base posterior end, a base anterior cavity disposed within proximal to the base anterior end, and a base posterior cavity disposed within proximal to the base posterior end, wherein the base anterior end comprises a keyhole disposed thereon for receiving the key, wherein the keyhole is fluidly connected to the base anterior cavity, wherein a barbed first key clamp operatively connected to a first solenoid is disposed in the base anterior cavity and outwardly biased via a first spring, wherein a barbed second key clamp operatively connected to a second solenoid is disposed in the base anterior cavity and outwardly biased via a second spring, wherein the base posterior end comprises a breathing aperture disposed on a tip thereon, wherein the breathing aperture is fluidly connected to the base posterior cavity, wherein the base posterior cavity comprises an alcohol sensor and a power supply each operatively connected to a microprocessor disposed therein, wherein the microprocessor is operatively connected to the first solenoid and the second solenoid, wherein the key is disposed in the base anterior cavity via the keyhole, wherein the key is slid into position and secured via the first spring biased barbed first key clamp interfacing with a key first side keycut and the second spring biased barbed second key clamp interfacing with a key second side keycut, wherein in a secured position the key is held in the base anterior cavity, via the first key clamp and the second key clamp clamping the key, wherein to release the key from the base anterior cavity a user breathes into the breathing aperture disposed in the base posterior cavity, wherein the alcohol sensor detects a blood alcohol content by volume in a breath of the user, wherein the microprocessor analyzes the blood alcohol content with respect to a blood alcohol limit, wherein if the blood alcohol content is below the blood alcohol content limit, the microprocessor sends a signal to the first solenoid and the second solenoid to retract for a period of time, wherein upon retraction of the first solenoid, the first key clamp slides away from the key first side keycut of the key, wherein upon retraction of the second solenoid, the second key clamp slides away from the key second side keycut, wherein the key is able to be pulled from the keyhole, wherein after a period of time, the first solenoid and the second solenoid release from a retracted position.

2. The system of claim 1, wherein the blood alcohol content limit is 0.05 by volume.

3. The system of claim 1, wherein the first key clamp and the second key clamp comprise barbs, wherein each barb comprises a sloped barb anterior side, and a perpendicular barb posterior side for slidably allowing an entrance of the key and for limiting an exit of the key unless the blood alcohol content is below the blood alcohol content limit.

* * * * *